United States Patent [19]

Seeler

[11] Patent Number: 4,508,112
[45] Date of Patent: Apr. 2, 1985

[54] FLUID PRESSURE ACTUATED IMMOBILIZING STRUCTURE

[76] Inventor: C. Oliver Seeler, P.O. Box 246, Albion, Calif. 95410

[21] Appl. No.: 510,462

[22] Filed: Jul. 1, 1983

[51] Int. Cl.³ .............................................. A61F 5/04
[52] U.S. Cl. ........................... 128/89 R; 128/DIG. 20
[58] Field of Search .......... 128/87 R, 89 R, DIG. 20, 128/83

[56] References Cited

U.S. PATENT DOCUMENTS

| | | | |
|---|---|---|---|
| 3,823,712 | 7/1974 | Morel | 128/87 R |
| 3,868,952 | 3/1975 | Hatton | 128/DIG. 20 |
| 4,169,467 | 10/1979 | Rabischong et al. | 128/89 R X |
| 4,263,905 | 4/1981 | Couch, Jr. | 128/DIG. 20 |

*Primary Examiner*—John D. Yasko

*Attorney, Agent, or Firm*—Townsend and Townsend

[57] ABSTRACT

A fluid pressure actuated immobilizing structure finds particular utility as a reusable, temporary emergency cast. The structure includes a flexible, nonexpandable outer container, a flexible, non-porous inner container and a pressure-sensitive matrix material. The matrix material and the inner container are both housed within the outer container. The matrix material is adapted to permit relatively unhindered relative movement among the matrix elements under normal conditions; the matrix material locks into a substantially rigid mass when squeezed together to freeze the immobilizing structure into the shape existing immediately before pressurization. Since the outer container does not expand, pressurizing the structure causes the structure to turn rigid without squeezing the patient.

10 Claims, 9 Drawing Figures

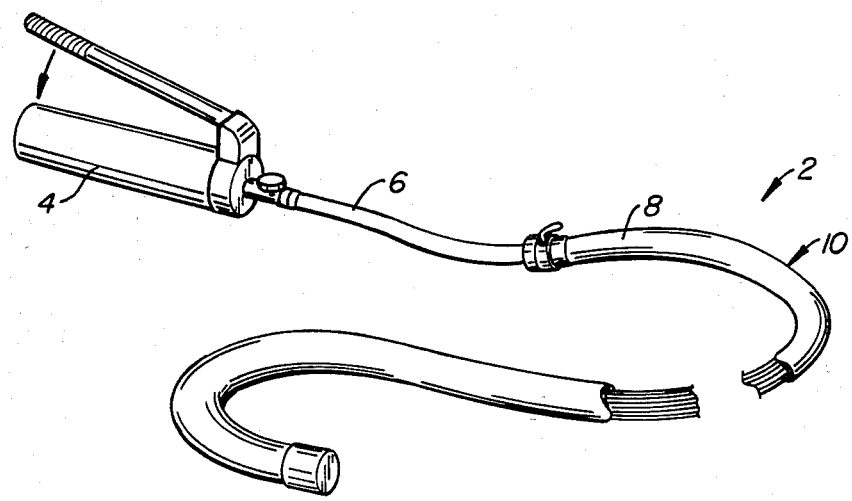
FIG._1.
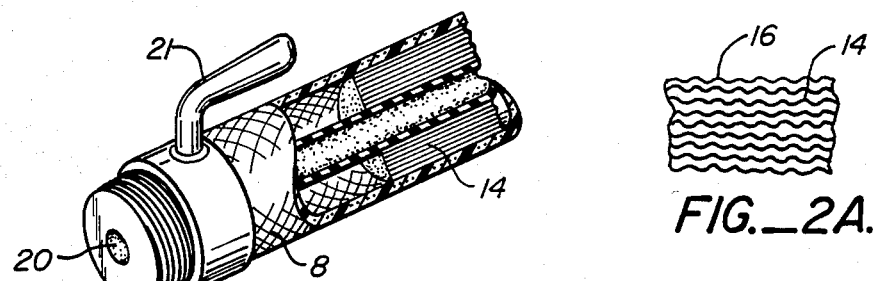
FIG._2.   FIG._2A.
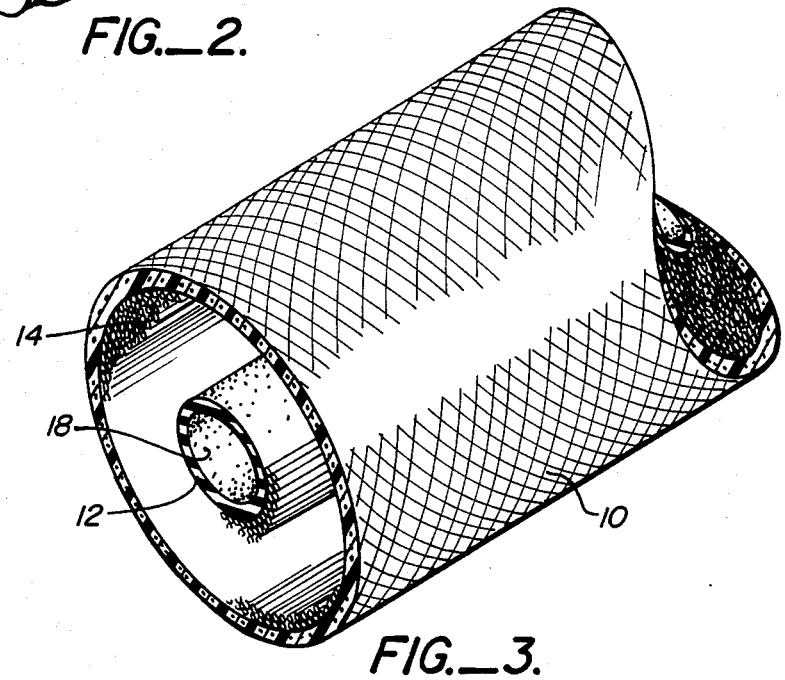
FIG._3.

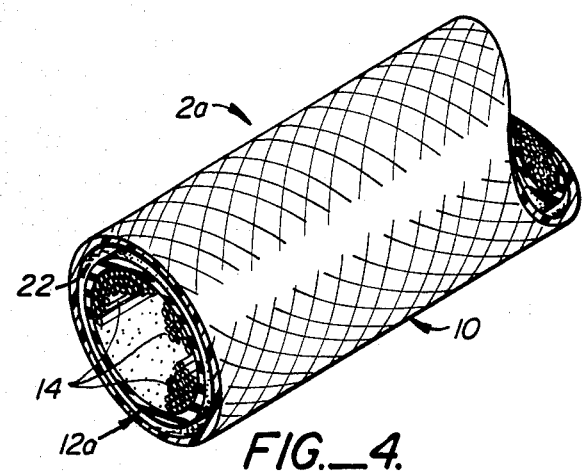
FIG._4.
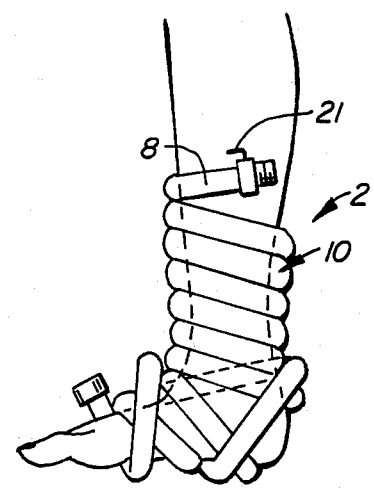
FIG._5.
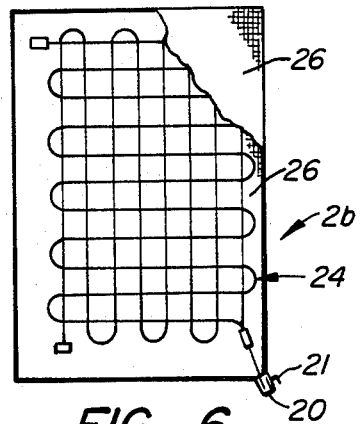
FIG._6.
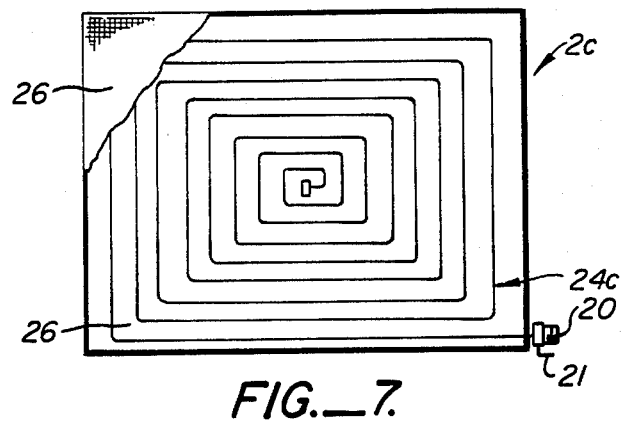
FIG._7.
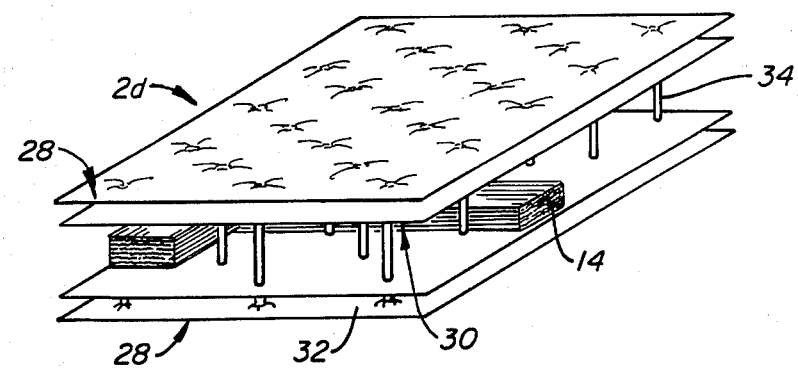
FIG._8.

FLUID PRESSURE ACTUATED IMMOBILIZING STRUCTURE

BACKGROUND OF THE INVENTION

Accident victims who have sustained serious injury usually must be transported to a medical facility to receive appropriate treatment. However, many injuries can be made worse if the victim is moved improperly. Therefore before moving an accident victim one usually attempts to immobilize the injured body parts. This is often done using various types of rigid splints pressed against the body with straps or other restraining devices. For example, see U.S. Pat. No. 4,211,218 to Kendrick. This patent shows a jacket-like device used to support the head, neck and back so the accident victim can be moved while restraining spinal movement. However, such immobilizing devices can be somewhat difficult to place on an accident victim without gross movements of the victim. Further, standard splint-type restraining devices using straps tend to squeeze the victim's body to in effect use the body as a structural element adding rigidity to the combination of the restraining device and the body part. This can cause further complications depending upon the type and extent of injury. Also, splints are often configured for use with specific body parts so many types must be carried by emergency first aid crews.

Another structure which could be used as a temporary splint is shown in U.S. Pat. No. 3,212,497 to Dickinson. This type of temporary splint uses a nonporous outer bag and a porous inner bag containing a mass of discrete particles. After being fitted to the injured body part, the outer bag is evacuated to allow the external atmospheric pressure to force the discrete particles against one another to form a rigid mass. The temporary splint is thus locked into the configuration, such as surrounding a patient's arm, it was in before the vacuum was applied to the outer bag. Although this type of temporary splint can be used with different body parts, it may tend to squeeze the patient when the vacuum is drawn. Also, the maximum pressure available for rigidifying the mass of discrete particles is atmospheric pressure; therefore such a splint may not be suitable when significant structural support is needed, such as when supporting an accident victim's head, neck and back. Also, vacuum actuated splints require the use of a vacuum pump, which are often not readily available.

Therefore, what has been missing in the prior art is a temporary splint which can be used to immobilize different body parts and which is strong enough to immobilize a patient's head, neck and back without squeezing the patient.

SUMMARY OF THE INVENTION

The present invention is directed to a fluid pressure actuated immobilizing structure finding particular utility as an emergency splint. The structure includes a flexible, but substantially nonexpandable, outer container, a flexible, non-porous inner container and a pressure-sensitive matrix material. The matrix material and the inner container are both housed within the outer container. The matrix material is adapted to permit relatively unhindered relative movement among the matrix elements under normal conditions, but to lock into a substantially rigid mass when the matrix material is compressed or squeezed.

The matrix material may be located within the inner container, or between the inner and outer containers. If located within the inner container, applying fluid pressure to the region between the inner and outer containers squeezes the inner container thus compressing the matrix material therein. This effectively locks the immobilizing structure into the shape existing immediately before pressurization. If the matrix material is located within the region between the inner and outer containers, fluid pressure is applied to the interior of the inner container which expands against the matrix material to squeeze the matrix material between the inner and outer containers. This locks the immobilizing structure into its pre-pressurized shape. Since the outer container does not expand, squeezing the matrix material causes it to turn rigid; however the structure does not press against or squeeze the body part wrapped within the immobilizing structure since the outer container is substantially nonexpandable.

A primary feature of the invention is the provision of the nonexpandable, flexible outer container which allows much greater force to be applied to the rigidifying matrix material than is available using vacuum systems such as that shown in the Dickinson patent. Also, since the outer container is essentially nonexpandable, upon pressurization the patient's body part being immobilized is not subjected to squeezing pressures as occurs with standard splints.

Another feature of the invention is the use of tubular outer and inner containers. This design allows a hose-like immobilizing structure to be used on a variety of body parts, rather than being specially adapted to, for example, the hand, forearm, or ankle. Thus excessive numbers of temporary splints, each adapted for a specific body part, are not needed.

Another feature of the invention is the use of elongate wires as the elements comprising the pressure sensitive matrix material. These elongate matrix elements are typically used with the tubular containers and extend parallel to the length of the tubes. The outer surfaces of the wires are configured to resist relative longitudinal movement when the components are squeezed against one another. For example, the outer surfaces can be grooved or ridged to provide a degree of mechanical interlock, in addition to normal surface friction, when the wires are pressed against one another. When squeezed together, the mechanical interlock and surface friction keeps the wires from sliding past one another; the wire matrix acts as a rigid mass locking the immobilizing structure into its pre-pressurized shape.

The pressurizing fluid used with the present invention can be a liquid or a gas. If a liquid, small, hand-operated hydraulic pumps can be used to easily and quickly apply very high pressures to the immobilizing device. Thus, pressures many times greater than atmospheric can be used to compress the immobilizing matrix material to insure a strong, rigid structure.

Another advantage of the present invention occurs when it is incorporated into a blanket-type mobilizing structure. In one blanket embodiment, one or more tubular immobilizing structures are arranged within a quilt or blanket-like structure. The tubes can be arranged in various patterns, such as a flat spiral, a flat random maze or a woven pattern using two sets of parallel tubes arranged transversely to one another. Such an immobilizing blanket can be used advantageously for placement around an accident victim requiring a large body area to be immobilized. However, after pressurization, the immobilizing blanket will not squeeze the victim, but rather will encase the victim in a conforming, rigid cocoon so that the body position can be maintained during transport to the hospital.

The invention has been described in terms of its use as a temporary splint or cast. However, it is to be understood that the invention is also suitable for immobilizing or positioning inanimate objects as well.

Other features and advantages of the invention will appear from the following description in which the preferred embodiments have been set forth in detail in conjunction with the accompanying drawings.

BRIEF DESCRIPTION OF THE DRAWINGS

FIG. 1 shows a tubular embodiment of the invention connected to a hydraulic hand pump.

FIG. 2 is an enlarged isometric view of the connection end of the embodiment of FIG. 1.

FIG. 2A is an enlarged view of a section of matrix wire.

FIG. 3 is an enlarged cross-sectional isometric view of the tubular embodiment of FIG. 1.

FIG. 4 is a cross-sectional isometric view of a second tubular embodiment of the invention.

FIG. 5 shows the embodiment of FIG. 1 wrapped around a person's lower leg and ankle.

FIG. 6 is a simplified plan view showing a blanket embodiment of the invention incorporating the tubular embodiment of FIG. 1 in a woven pattern.

FIG. 7 is a simplified plan view of a second blanket embodiment with a tubular immobilizing structure wound in a flat spiral.

FIG. 8 is a partial cross-sectional view of a further immobilizing blanket embodiment of the invention.

DETAILED DESCRIPTION OF THE PREFERRED EMBODIMENTS

Turning now to FIGS. 1, 2, and 3, a first, tubular embodiment of a fluid pressure actuated immobilizing structure 2 of the invention is shown connected to a hydraulic hand pump 4 by a flexible hose 6 at the connection end 8 of structure 2. Structure 2 includes a flexible, nonexpandable outer tube 10, a flexible, nonporous, expandable inner tube 12 and a plurality of elongate wires 14 arranged within the region between the outer and inner tubes 10, 12. The outer surfaces of wires 14 are formed with numerous annular grooves 16 as shown in FIG. 2a. Wires 14 comprise a pressure sensitive rigidifying matrix as described in more detail below.

The interior 18 of inner tube 12 is sealed with the exception of a fluid port 20 formed at connection end 8. Fluid port 20 permits connection of immobilizing structure 2 to hand pump 4 via hose 6 to allow interior 18 to be pressurized. Fluid port 20 is sealed by manipulation of a valve handle 21.

Outer tube 10, inner tube 12 and wires 14 are all flexible to allow structure 2 to be wrapped around various body parts when inner tube is not pressurized. For example, FIG. 5 shows structure 2 wrapped around the person's lower leg, ankle and foot. As illustrated in FIG. 2, wires 14 do not extend the entire length of outer tube 10; when structure 2 is flexed, individual wires 14 can slip longitudinally past one another according to the various bend radii along their lengths caused by changes in the shape of structure 2.

To lock structure into its pre-pressurization state, hose 6 is connected to end 8 and valve handle 21 is turned to an open position. Pump 4 is operated to force pressurized fluid into interior 18. This causes inner tube 12 to expand and press against wires 14 squeezing them against one another between inner tube 12 and outer tube 10. The roughened outer surfaces of wires 14 become interlocked upon the application of such force. Under the effects of surface friction and mechanical interlock, wires 14 can no longer slip past one another, as is necessary for the unrestrained flexing of structure 2. Therefore, structure 2 becomes locked into its pre-pressurization shape. Since outer tube 10 is substantially nonexpandable, structure 2 does not squeeze the patient's body; instead structure 2 acts as a rigid temporary cast supplying support to the patient without using the patient's body as a structural element, as is required with prior art splint-type restraining devices. After pressurization valve handle 21 is tuned to seal port 20 and hose 6 is disconnected from structure 2 so the patient can be transported. To remove structure 2, valve handle 21 is turned to open port 20 to allow the pressurized fluid to escape. This causes structure 2 to once again become flexible for easy removal. If the pressurizing fluid is a liquid, a suitable line and reservoir can be attached to end 8 to catch the discharged liquid.

A second embodiment of the invention is shown in FIG. 4. It is similar to the embodiment of FIG. 3 but differing in that wires 14 are housed within a flexible, collapsible inner tube 12a. The pressurized fluid is supplied to a region 22 between inner tube 12a and outer tube 10. In this embodiment, wires 14 are squeezed against one another by the constriction of inner tube 12a.

FIG. 6 shows a further embodiment in the form of a blanket. Structure 2b includes a pair of tubular elements 24 woven into a transverse grid and sandwiched between and attached to sheets of material 26. Tubular elements 24 are constructed in the same manner as structure 2 of FIG. 1. Tubular elements 24 are connected to common fluid port 20 for connection to hose 6. Immobilizing blanket structure 2b can be wrapped around a person with possible neck or back injuries. After blanket structure 2b is in position, tubular elements 24 are pressurized through fluid port 20 to lock structure 2b into its pre-pressurized shape. Valve handle 21 is then closed, sealing the pressurized fluid within tubular elements 24 so that hose 6 can be disconnected from fluid port 20 to allow the person to be transported.

FIG. 7 shows a second blanket immobilizing structure 2c similar to the blanket mobilizing structure 2b of FIG. 6. In this embodiment, tubular element 24c is mounted between and attached to sheets of material 26 in a generally rectangular, spiral pattern. In both the embodiments of FIG. 6 and FIG. 7 the tubular elements are positioned so that no hinge lines, that is regions at which there is no substantial resistance to bending, exist. Other patterns of tubular elements can also be used.

FIG. 8 shows a further blanket immobilizing structure 2d which includes an outer container 28 and inner container 30. Outer and inner containers are flexible and non-porous. Wires 14 are housed within inner container 30 in a transverse pattern. Fluid pressure is applied to a region 32 between outer and inner containers 28, 30 thereby squeezing wires 14 against one another to keep the blanket in its pre-pressurized shape. Outer container 28 remains essentially nonexpandable under the application of pressure within region 32 through the use of numerous stays 34. These stays are flexible, but very strong to be substantially non-stretchable in tension so that pressurization of structure 2d causes outer container 28 to assume a quilted or dimpled appearance. Stays 34 are spaced closely enough so that during use immobilizing blanket structure 2d does not squeeze the patient to any substantial degree when pressurized. In lieu of inner container 30, a number of inner tubes 12a, with wires 14 therein, may be mounted within outer container 28 and between stays 34.

Modification and variation can be made to disclosed embodiments without departing from the subject of the invention as defined in the following claims. For example, other pressure sensitive matrix materials, such as the granular material disclosed for use in U.S. Pat. No. 3,212,417 to Dickinson, be used instead of wires 14. Also wires 14 can have their surfaces configured in a variety of shapes, contours and textures depending upon the particular applications and pressures to be used. For example, for lower pressure situations it may be desirable to use wires having a toothed-shaped surface to provide sufficient resistance to relative longitudinal movement once immobilizing structure 2 is pressurized. Also, it may be desired to vent the region containing the matrix material to increase the effectiveness of the fluid pressure applied to it.

I claim:

1. A fluid pressure actuated immobilizing structure comprising:
   a flexible, substantially nonexpandable outer container;
   a pressure sensitive matrix material situated within said outer container, said matrix material adapted to permit relatively unhindered relative movement among the elements comprising said matrix material under normal conditions and to substantially inhibit relative movement among the matrix elements when the matrix elements are squeezed together; and
   fluid pressurization means for squeezing said pressure sensitive matrix material thereby compressing said matrix material to lock the immobilizing structure into the shape existing immediately before pressurization.

2. A fluid pressure actuated immobilizing structure comprising:
   a flexible, substantially nonexpandable outer container;
   a flexible, expandable, non-porous inner container housed within said outer container;
   a pressure sensitive matrix material situated between said outer and inner containers, said matrix material adapted to permit relatively unhindered relative movement among the elements comprising said matrix material under normal conditions and to substantially inhibit relative movement among the matrix elements when the matrix elements are squeezed together; and
   a fluid port for introducing pressurized fluid into said inner container thereby expanding said inner container to squeeze said pressure sensitive matrix material between said inner and outer containers thereby compressing said matrix material to lock the immobilizing structure into the shape existing immediately before pressurization.

3. A fluid pressure actuated immobilizing structure comprising:
   a flexible, substantially nonexpandable, non-porous outer container;
   a flexible, collapsible, non-porous inner container housed within said outer container;
   a pressure sensitive matrix material situated within said inner container, said matrix material adapted to permit relatively unhindered relative movement among the elements comprising said matrix material under normal conditions and to substantially inhibit relative movement among the matrix elements when the matrix elements are squeezed together; and
   a fluid port for introducing pressurized fluid into a pressurization region between said outer and inner containers thereby squeezing said inner container and said pressure sensitive matrix material therein to lock the immobilizing structure into the shape existing immediately before pressurization.

4. The immobilizing structure of claims 1 or 2 or 3 wherein said outer container is a generally cylindrical, elongate tube.

5. The immobilizing structure of claim 1 wherein said fluid pressurization means includes a flexible, deformable, non-porous inner container housed within said outer container.

6. The immobilizing structure of claims 2, 3, or 5 wherein said inner tube is an elongate cylindrical tube.

7. The immobilizing structure of claims 2 or 3 wherein said matrix material includes generally granular material.

8. The immobilizing structure of claims 2 or 3 wherein said matrix material includes elongate strands, the outer surface of said strands exhibiting pressure sensitive frictional characteristics to hinder relative sliding movement when biased against one another.

9. The immobilizing structures of claim 8 wherein said outer strand surfaces are roughened.

10. The immobilizing structures of claim 8 wherein said outer strand surfaces include circular grooves.

* * * * *